(12) United States Patent
Goedecke

(10) Patent No.: US 9,147,565 B1
(45) Date of Patent: Sep. 29, 2015

(54) ION MOBILITY SPECTROMETER AND METHOD OF USING THE SAME

(71) Applicant: MORPHO DETECTION, LLC, Newark, CA (US)

(72) Inventor: Lyndon Karl Goedecke, Everett, MA (US)

(73) Assignee: MORPHO DETECTION, LLC, Newark, CA (US)

( * ) Notice: Subject to any disclaimer, the term of this patent is extended or adjusted under 35 U.S.C. 154(b) by 0 days.

(21) Appl. No.: 14/586,503

(22) Filed: Dec. 30, 2014

(51) Int. Cl.
*B01D 59/44* (2006.01)
*H01J 49/00* (2006.01)
*H01J 49/28* (2006.01)
*H01J 49/40* (2006.01)
*H01J 49/02* (2006.01)
*G01N 27/62* (2006.01)

(52) U.S. Cl.
CPC ............ *H01J 49/022* (2013.01); *G01N 27/622* (2013.01)

(58) Field of Classification Search
USPC ......... 250/281–283, 285–288, 290, 292, 294, 250/299
See application file for complete search history.

(56) References Cited

U.S. PATENT DOCUMENTS

| | | | |
|---|---|---|---|
| 3,256,444 A | 6/1966 | Jones et al. | |
| 4,797,554 A * | 1/1989 | Blanchard et al. | 250/287 |
| 5,021,654 A * | 6/1991 | Campbell et al. | 250/287 |
| 5,095,206 A * | 3/1992 | Bacon et al. | 250/282 |
| 5,200,614 A | 4/1993 | Jenkins | |
| 5,491,337 A | 2/1996 | Jenkins et al. | |
| 5,570,180 A | 10/1996 | Nagai | |
| 5,834,771 A * | 11/1998 | Yoon et al. | 250/286 |
| 6,690,005 B2 | 2/2004 | Jenkins et al. | |
| 6,765,198 B2 | 7/2004 | Jenkins et al. | |
| 6,831,272 B2 | 12/2004 | Mack et al. | |
| 7,078,675 B2 | 7/2006 | Zastrow et al. | |
| 7,087,897 B2 | 8/2006 | Bateman et al. | |
| 7,105,808 B2 * | 9/2006 | Bromberg et al. | 250/287 |
| 7,538,320 B2 | 5/2009 | Sperline | |

(Continued)

FOREIGN PATENT DOCUMENTS

| EP | 0456700 B1 | 4/1995 |
|---|---|---|
| EP | 1178307 A1 | 2/2002 |

(Continued)

OTHER PUBLICATIONS

GE Security, Ion Trap Mobility Spectrometry: The Science Behind the Technology, 2008, 6 pages, GE Homeland Protection, Inc.

*Primary Examiner* — Bernard E Souw
(74) *Attorney, Agent, or Firm* — Armstrong Teasdale LLP

(57) ABSTRACT

A method of detecting constituents in a sample includes generating a plurality of ions in an ionization region. The method also includes preventing the plurality of ions in the ionization region from flowing into a drift region through inducing a first voltage in a device positioned between the two regions. The method further includes injecting at least a portion of the ions from the ionization region into the drift region. The method also includes regulating the voltage in the device to a second voltage for a first predetermined temporal period, the second voltage less than the first voltage. The method further includes regulating the voltage in the device to the first voltage. The method also includes regulating the voltage in the device to the second voltage for a second predetermined temporal period, the second predetermined temporal period different from the first predetermined temporal period.

20 Claims, 3 Drawing Sheets

(56) References Cited

U.S. PATENT DOCUMENTS

| | | | |
|---|---|---|---|
| 8,866,073 B2 * | 10/2014 | Goedecke | 250/282 |
| 2002/0005479 A1 | 1/2002 | Yoshinari et al. | |
| 2005/0205775 A1 * | 9/2005 | Bromberg et al. | 250/290 |
| 2006/0163472 A1 | 7/2006 | Marquette | |
| 2007/0158548 A1 | 7/2007 | Haigh | |
| 2008/0087818 A1 | 4/2008 | Li | |
| 2008/0179515 A1 | 7/2008 | Sperline | |
| 2014/0264002 A1 * | 9/2014 | Goedecke | 250/282 |

FOREIGN PATENT DOCUMENTS

| | | |
|---|---|---|
| EP | 1271610 A2 | 1/2003 |
| WO | 8805535 A2 | 7/1988 |
| WO | 2012148836 A1 | 11/2012 |

* cited by examiner

ION MOBILITY SPECTROMETER AND METHOD OF USING THE SAME

BACKGROUND

The embodiments described herein relate generally to an ion mobility spectrometer (IMS) and, more particularly, to an IMS detection system for enhancing detection of materials of interest through enhanced resolution of high-mobility ions and low-mobility ions.

At least some known spectroscopic detection devices include a time-of-flight (TOF) ion mobility spectrometer (IMS) detection system. Such TOF-IMS detection systems are used to detect trace portions of materials of interest, e.g., residues, in the presence of interfering substances in collected samples. In at least some known TOF-IMS detection systems, ions are generated in an ionization region to increase the ion population therein. An ion gate (sometimes referred to as an ion shutter) that includes a conducting grid of interleaved wires, e.g., a Bradbury-Nielson gate, is maintained in a "cut-off" condition that is configured to prevent an ion current to transmit from the ionization region. Energizing the ion gate deflects the ions in the ionization region to the gate wires, thereby collecting the ions and preventing them from flowing through the gate. De-energizing the ion gate allows the ions to flow out from the ionization region into a drift region, where a time-of-flight spectrum is generated. Based on an ions' mass, charge, size, and shape (the ion mobility), the migration time through the drift region is characteristic of different ions, leading to the ability to distinguish different analyte species.

The population of ions generated in the ionization region include low-mobility analytes and high-mobility analytes. The low-mobility analytes traverse the drift region with a lower velocity than the high-mobility analytes due to their relatively larger molecular size than the high-mobility analytes. The low-mobility and high-mobility analytes pulsed into the drift region from the ionization region typically generate spectrum peaks on spectral analysis equipment.

Both the sensitivity associated with the amplitude of the peaks (for low-level detection) and resolving power associated with the width of the peaks (to distinguish between close spectrum peaks) of the instrument are important. The ion gating time is the temporal period that the ion gate is de-energized. The resolving power for any particular analyte increases as the gating time is reduced because the initial peak width decreases. The increased resolving power and the associated narrower peak widths facilitate improved detection resolution. Notably, the sensitivity decreases rapidly below a certain ion gating time, thereby defining a lower limit for the ion gating time for an ion species of given mobility.

Ions of lower mobility and longer drift times have wider spectrum peak widths as a function of diffusion in the axial direction along the drift region as compared to higher mobility ions with shorter drift times. Therefore, for the same gating injection time and same initial ion current in the source region, the peak heights for the lower mobility ion have smaller values as compared to higher mobility ions. The lower mobility ions will exhibit higher spectrum peaks, i.e., increased sensitivity with a longer gating pulse. The higher mobility ions will also have higher spectrum peaks with longer gating pulses, but a significantly lower resolving power will result, thereby decreasing the resolution of the spectrum peaks. Therefore, the optimum ion gating time is different for every analyte mobility peak and the optimum ion gating time should be proportional to the drift time of a particular ion. As such, since known general purpose TOF-IMS systems need to sample ions of many species, often simultaneously, the sensitivity and the resolving power for a range of analytes during the period of a sample, usually 3-10 seconds, are not optimized for each of the analytes. Specifically, resolution of spectral traces of high-mobility analytes is sacrificed for retaining sensitivity for low-mobility analytes.

BRIEF DESCRIPTION

In one aspect, a method of detecting constituents in a sample is provided. The method includes channeling a sample gas stream to be tested for constituents into an ionization region and generating a plurality of ions in the ionization region. The method also includes substantially preventing the plurality of ions in the ionization region from flowing into a drift region coupled to the ionization region through inducing a first voltage in a device positioned between the ionization region and the drift region. The method further includes injecting at least a portion of the ions from the ionization region into the drift region including regulating the voltage in the device to a second voltage for a first predetermined temporal period. The second voltage is less than the first voltage. The method also includes regulating the voltage in the device to the first voltage and regulating the voltage in the device to the second voltage for a second predetermined temporal period. The second predetermined temporal period is different from the first predetermined temporal period.

In another aspect, an apparatus for detecting constituents in a sample is provided. The apparatus includes a casing, an ionization region at least partially defined by the casing, and a drift region at least partially defined by the casing. The ionization region is configured to generate ions. The apparatus also includes an ion gate device positioned between the ionization region and the drift region. The ion gate device is configured to facilitate prevention of the plurality of ions in the ionization region from flowing into the drift region through inducing a first voltage in the ion gate device. The apparatus further includes a control system coupled to the ionization chamber. The control system includes a processor. The control system is configured to regulate the voltage in the ion gate device to a second voltage for a first predetermined temporal period and inject a first portion of the ions from the ionization region into the drift region. The second voltage is less than the first voltage. The control system is also configured to regulate the voltage in the ion gate device to the first voltage. The control system is further configured to regulate the voltage of the ion gate device to the second voltage for a second predetermined temporal period and inject a second portion of the ions from the ionization region into the drift region. The second predetermined temporal period is different from the first predetermined temporal period.

In yet another aspect, one or more computer readable storage media having computer-executable instructions embodied thereon is provided. When executed by at least one processor, the computer-executable instructions cause the processor to regulate a voltage generated in an ion gate device to a first voltage. The ion gate device is positioned between an ionization region and a drift region in an ion mobility spectrometer (IMS) detection system, thereby facilitating prevention of a plurality of ions flowing from the ionization region. Also, when executed by at least one processor, the computer-executable instructions cause the processor to regulate the voltage generated in the ion gate device to a second voltage for a first predetermined temporal period, the second voltage is less than the first voltage, thereby facilitating injection of a first portion of the ions from the ionization region into the drift region. Further, when executed by at least one processor, the computer-executable instructions cause the processor to regulate the electric field to back to the first voltage. Moreover, when executed by at least one processor, the computer-executable instructions cause the processor to regulate the electric field to the second voltage for a second predetermined temporal period, thereby facilitating injection of a second portion of the ions from the ionization region into the drift region, the second predetermined temporal period is different from the first predetermined temporal period.

DRAWINGS

FIG. 1 is a schematic view of an exemplary time-of-flight (TOF) ion mobility spectrometer (IMS) detection system;

Figure 1:
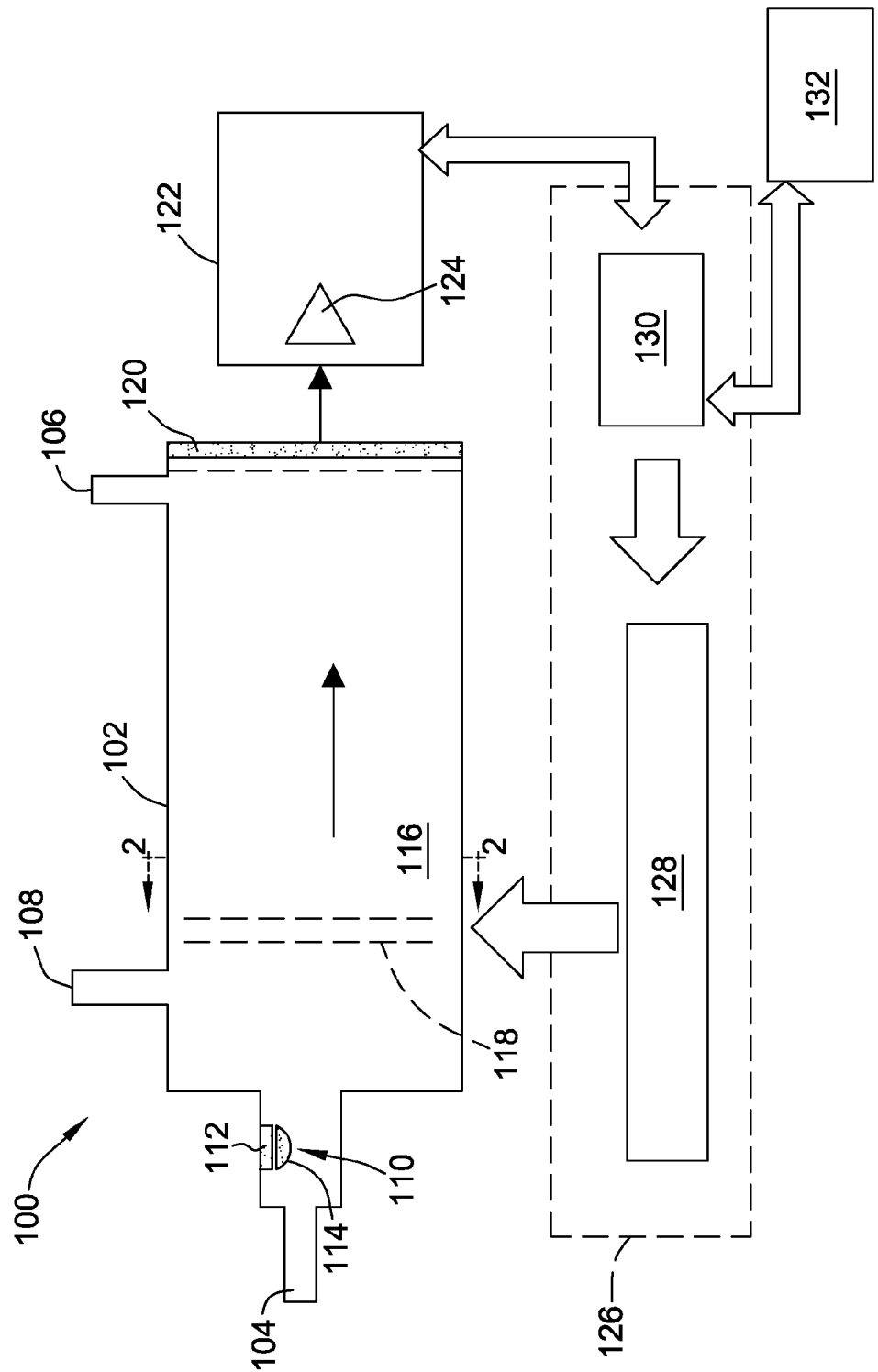
FIGS. 1-3 show exemplary embodiments of the systems and methods described herein.
Figure 2:
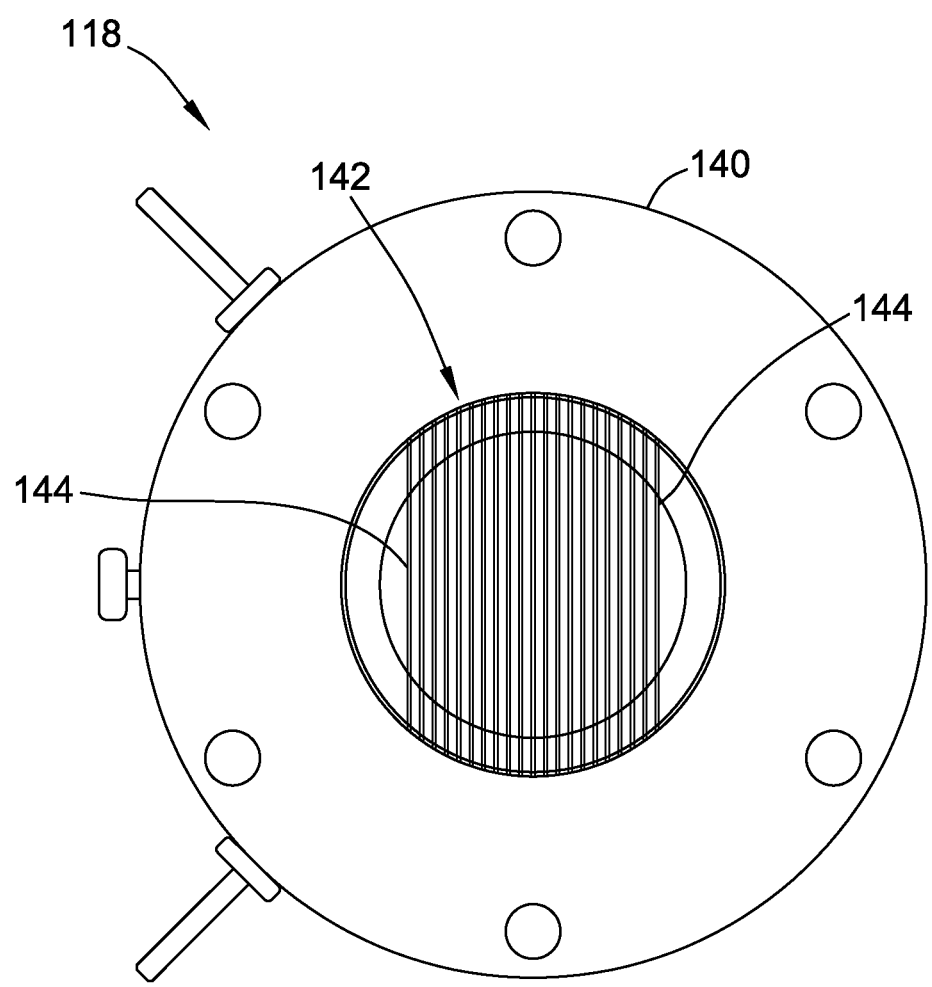
Figure 3:
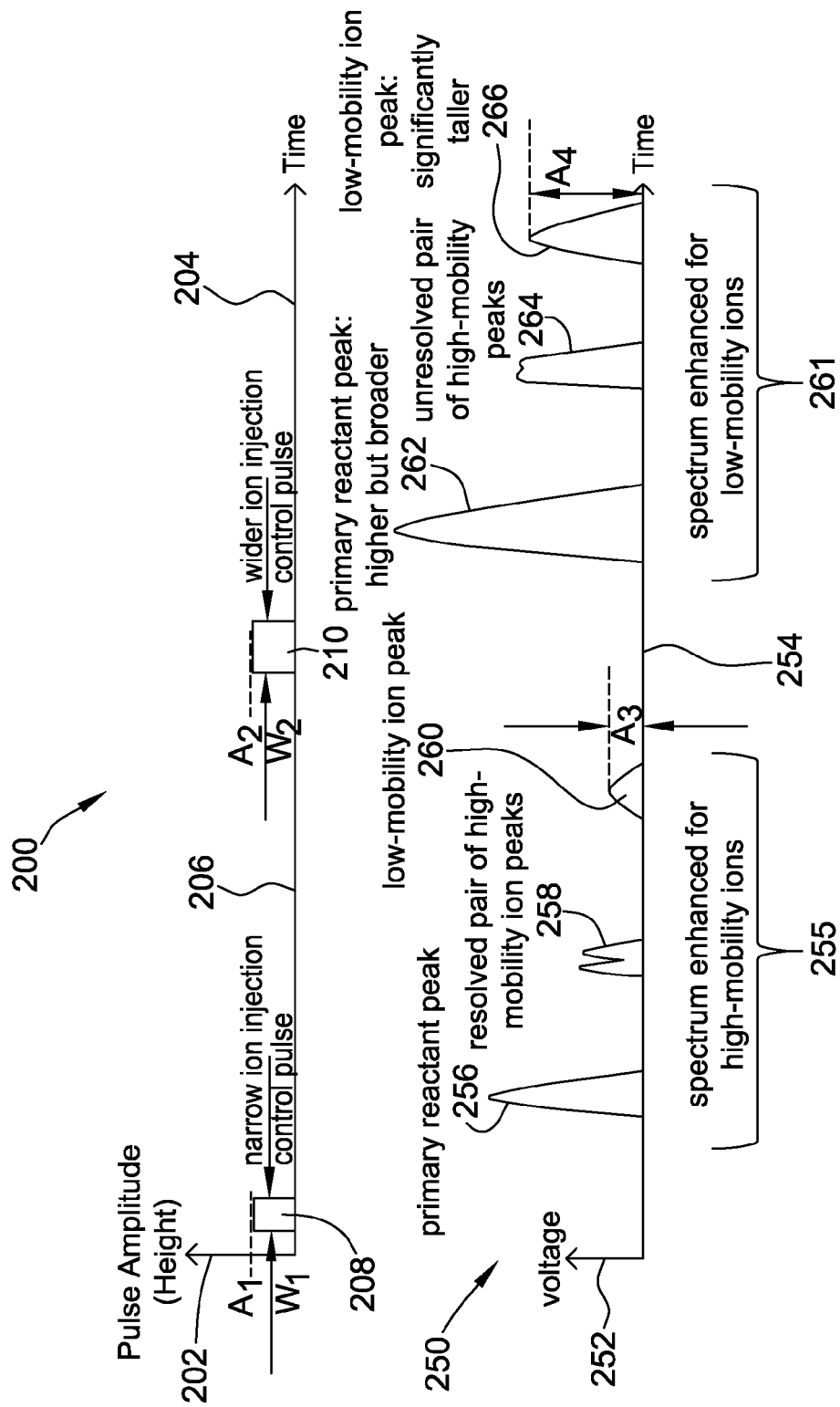

FIG. 2 is a schematic view of an exemplary ion gate device that may be used with the TOF-IMS detection system shown in FIG. 1 taken about line 2-2 shown in FIG. 1; and FIG. 3 is a graphical view of exemplary ion injection pulse control voltage waveforms for fast ions and slow ions that may be used with the TOF-IMS detection system shown in FIG. 1 and resultant spectra enhanced for high-mobility and low-mobility ions.

DETAILED DESCRIPTION

The embodiments described herein provide a cost-effective system and method for improving detection of materials of interest from an object or person. The systems and methods described herein use two different pulse widths to inject ions from an ionization region into a drift region during de-energization of an ion gate device. The first, i.e., narrower pulse width facilitates de-energizing the ion gate device for a shorter temporal period, thereby enhancing detection of high-mobility ions through generating a first spectral trace including a plurality of resolved high-mobility ion peaks. As such, resolution of spectral traces of high-mobility analytes is enhanced. The same first spectral trace includes a low-mobility ion peak having a first amplitude. The second, i.e., wider pulse width facilitates de-energizing the ion gate device for a longer temporal period, thereby enhancing detection of low-mobility ions through generating a spectral trace including a low-mobility ion peak having a second amplitude greater than the first amplitude. As such, sensitivity for low-mobility analytes is also enhanced.

FIG. 1 is a schematic view of an exemplary time-of-flight (TOF) ion mobility spectrometer (IMS) detection system 100. TOF-IMS detection system 100 includes a casing 102. IMS detection system 100 also includes a sample inlet tube 104, a drift gas inlet tube 106, and a gas outlet tube 108 coupled to casing 102. Casing 102 defines a ionization region 110 coupled in flow communication with sample inlet tube 104. Ionization region 110 includes an ionizing source material, i.e., a radioactive source 112, e.g., and without limitation, nickel-63 ($^{63}$Ni) that emits low-energy beta- ($\beta$-) particles to generate ions 114. Alternatively, any ionizing source material that enables operation of IMS detection system 100 as described herein is used. Further, alternatively, any method of ionization is used that enable operation of IMS system 100 as described herein, including, without limitation, an electron beam source. Casing 102 further defines a drift region 116 coupled in flow communication with ionization region 110.

IMS detection system 100 further includes an ion gate device 118 (sometimes referred to as an ion shutter) extending over an outlet end of ionization region 110 and inlet end of drift region 116.

FIG. 2 is a schematic view of ion gate device 118 that may be used with TOF-IMS detection system 100 (shown in FIG. 1) taken about line 2-2 (shown in FIG. 1). Ion gate device 118 is a Bradbury-Nielson gate that includes a ceramic frame element 140 shaped and configured to facilitate the transition between ionization region 110 and drift region 116 (both shown in FIG. 1). Ion gate device 118 also includes a conducting gate 142 of interleaved wires 144 with predetermined voltages induced between adjacent wires 144. In the exemplary embodiment, interleaved wires 144 are substantially parallel to each other with a 0.7 millimeter (mm) spacing therebetween and a diameter of approximately 0.5 mm each. Alternatively, gate 142 has any configuration of wires 144 that enable operation of ion gate device 118 and TOF-IMS detection system 100 as described herein, including, without limitation, screens with substantially perpendicular criss-crossing wires and overlapping serpentine wires. Also, alternatively, any ion gate device that enables operation of IMS detection system 100 as described herein is used.

Referring to FIGS. 1 and 2, as ions 114 are generated in ionization region 110 to increase the ion population therein, wires 144 of ion gate device 118 are maintained at a predetermined relative potential to collect substantially all ion flow and substantially prevent leakage of ions 114 from ionization region 110 into drift region 116.

IMS detection system 100 also includes an ion detector 120 (sometimes referred to as an "ion collector") positioned opposite ion gate device 118 in drift region 116. Ion detector 120 is coupled to a spectral analysis device 122 that includes at least one electronic current-to-voltage amplifier 124. IMS detection system 100 also includes an IMS control system 126 that includes a pulse control device 128 and a processing device 130. Pulse control device 128 is coupled to ion gate device 118. Processing device 130 is operatively coupled to spectral analysis device 122 and pulse control device 128.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device.

Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Processing device 130 and other processors (not shown) as described herein process information transmitted from a plurality of electrical and electronic devices that include, without limitation, spectral analysis device 122 and pulse control device 128. Memory devices (not shown) and storage devices (not shown) store and transfer information and instructions to be executed by processing device 130. Such memory devices and storage devices can also be used to store and provide temporary variables, static (i.e., non-volatile and non-changing) information and instructions, or other intermediate information to processing device 130 during execution of instructions by processing device 130. Instructions that are executed include, but are not limited to, analysis of signals transmitted from spectral analysis device 122. The execution of sequences of instructions is not limited to any specific combination of hardware circuitry and software instructions. IMS detection system 100 also includes a data storage device 132 coupled to processing device 130. Data storage device 132 stores the data generated by processing device 130, such data also retrievable through processing device 130.

In operation, a collection device (not shown) is coupled to sample inlet tube 104 and collects gaseous samples (not shown) from an object of interest (not shown). In some embodiments, rather than gaseous samples, inlet tube 104 channels particulate samples that are then vaporized to generate the gaseous samples. The gaseous samples are channeled into ionization region 110. $^{63}$Ni emits low-energy β-particles into ionization region 110 and the β-particles ionize the gaseous samples while in the gaseous phase, thereby forming positive ions and negative ions. There is a substantially constant electric field between sample inlet 104 and ion gate 118. Therefore, increasing the current of the ions within ionization region 110 is facilitated as a function of the flux of β-particles. As the ions are being generated in ionization region 110 to increase the ion current therein, wires 144 of ion gate device 118 are maintained at a relative voltage great enough to substantially prevent ion current into drift region 116.

The relative voltage difference between wires 144 of ion gate device 118 is then temporarily removed and ions 114 are pulsed from ionization region 110 into a drift region 116 through ion gate device 118. The temporal period of gate de-energization is defined by a pulse length (not shown in FIG. 1). The voltage applied between wires 144 of ion gate device 118 is re-established, thereby substantially halting ion entry from ionization region 110 into drift region 116. A second pulse follows to facilitate another injection of ions from ionization region 110 into drift region 116. The pulses are controlled through IMS control system 126 and are described further below.

Drift region 116 extends from ion gate device 118 to the region defined by detector 120. Motion is induced in the ions as they exit ionization region 110 into drift region 116 when ion gate device 118 is de-energized and the ions are channeled through drift region 116 to detector 120 by a constant electric field applied between gate 118 and detector 120. Signals representative of the ion population at detector 120 are generated and transmitted to spectral analysis device 122 to determine the constituents in the collected gas samples.

The population of ions generated in ionization region 110 includes low-mobility analytes and high-mobility analytes. The low-mobility analytes traverse drift region 116 with a lower velocity than the high-mobility analytes due to the relatively greater molecular size of the low-mobility analytes as compared to the high-mobility analytes.

FIG. 3 is a graphical view of de-energization pulse control voltage waveforms, i.e., pulses 200 for fast ions and slow ions that may be used with TOF-IMS detection system 100 (shown in FIG. 1) and resultant spectra 250 enhanced for high-mobility and low-mobility ions.

Pulses 200 are plotted with respect to a y-axis 202 that represents a pulse amplitude, i.e., height, and with respect to an x-axis 204 that represents time. A pulse-free region 206 represents no pulses and ion gate device 118 (shown in FIG. 1) is energized to induce a voltage between wires 144 of gate 142 (both shown ion FIG. 2). In this condition, wires 144 have a first relative voltage that facilitates maintaining ions 114 within ionization region 110.

A first ion injection pulse 208 is transmitted from pulse control device 128 to ion gate device 118 as commanded by processing device 130. First ion injection pulse 208 has a first pulse width $W_1$ corresponding to a first temporal period on time axis 204. First ion injection pulse 208 also has a first pulse amplitude $A_1$ that is representative of the second voltage induced in ion gate device 118, that in the exemplary embodiment is substantially regulated to zero, i.e., ion gate device 118 is substantially de-energized. Alternatively, the second voltage induced in ion gate device 118 has any value that enables operation of IMS detection system 100 as described herein.

A second ion injection pulse 210 is transmitted from pulse control device 128 to ion gate device 118 as commanded by processing device 130. Second ion injection pulse 210 has a second pulse width $W_2$ corresponding to a second temporal period on time axis 204. A value of second pulse width $W_2$ is greater than a value of first pulse width $W_1$, i.e., second ion injection pulse 210 is wider than first ion injection pulse 208. Second ion injection pulse 210 also has a second pulse amplitude $A_2$ that is representative of the second voltage induced in ion gate device 118, that in the exemplary embodiment is substantially regulated to zero, i.e., ion gate device 118 is substantially de-energized. Alternatively, the second voltage induced in ion gate device 118 has any value that enables operation of IMS detection system 100 as described herein.

Resultant detection spectra 250, representative of ions detected at ion detector 120, and enhanced for high-mobility and low-mobility ions, are shown in relation to pulses 208 and 210. Spectra 250 are plotted with respect to a y-axis 252 that represents voltage amplitude and with respect to an x-axis 254 that represents time.

In the exemplary embodiment, a first spectral trace 255 enhanced for high-mobility ions includes three spectral traces shown associated with pulse 208, i.e., a first primary reactant peak 256, a resolved pair of high-mobility ion peaks 258, and a first low-mobility ion peak 260 having an amplitude of $A_3$.

Also, in the exemplary embodiment, a second spectral trace 261 enhanced for low-mobility ions includes three spectral traces shown associated with pulse 210, i.e., a second primary reactant peak 262, an unresolved pair of high-mobility ion peaks 264, and a second low-mobility ion peak 266 having an amplitude of $A_4$.

Comparing first spectral trace 255 and second spectral trace 261, second primary reactant peak 262 has greater amplitude and is temporally broader than first primary reactant peak 256. Such effect is substantially due to de-energizing ion gate device 118 for a longer period of time through pulse 210 as compared to pulse 208. Also, the pair of peaks of resolved of high-mobility ion peaks 258 are clearly distinguished while the pair of peaks are difficult to determine in unresolved pair of high-mobility ion peaks 264.

For a TOF-IMS instrument of a given geometry and drift field intensity, a significant operating parameter affecting the resolving power and the sensitivity is the associated ion gating time. The ion gating time is the temporal period that ion gate device 118 is de-energized. In general, the resolving power is directly proportional to the drift time and inversely proportional to the peak width. Therefore, the resolving power increases with increasing drift time of the analytes and decreasing pulse width. Conversely, the drift times are associated with the molecular size of the analytes and are not directly affected by the ion gating time. As such, the effect shown between peaks 256 and 262 is primarily due to the smaller, higher-mobility ions of differing materials with a relatively small difference in their sizes being temporally separated during transport through drift region 116 when narrow injection pulse 208 is used as compared to when they are somewhat wider and overlap more such as when wider injection pulse 210 is used.

Also, an additional requirement for enhancing resolution of the high-mobility analytes is that the impulse response of electronic current-to-voltage amplifier 124 (shown in FIG. 1) handling the signal from ion detector 120 (shown in FIG. 1) must be significantly faster than the temporal duration of their associated peak widths.

Further, second low-mobility ion peak 266 is distinguished from first low-mobility ion peak 260, where second low-mobility ion peak 266 is substantially equal in width to first low-mobility ion peak 260, but has a greater amplitude, i.e., amplitude $A_4$ is greater than amplitude $A_3$. This effect is primarily due to the extended width of second pulse 210, as compared to first pulse 208, yet still substantially narrower than the diffusion-broadened widths of peaks 260 and 266, injecting a larger number of lower-mobility ions into drift region 116. In general, the lower mobility ions will exhibit higher spectrum peaks, i.e., increased sensitivity with a longer gating pulse, but without significantly reducing the resolving power, as long as the peak broadening due to diffusion significantly exceeds the initial peak width due to the injection time.

Referring to FIGS. 1, 2, and 3, in operation, ions 114 are generated in ionization region 110 as described above. Ion gate device 118 is energized with a relative voltage between wires 144 to substantially prevent ion leakage from ionization region 110 into drift region 116. As such, ions 114 exist only in ionization region 110.

Also, in operation, first ion injection pulse 208 is transmitted from pulse control device 128 to ion gate device 118 as commanded by processing device 130. First ion injection pulse 208 has a first pulse width $W_1$ corresponding to a first temporal period on time axis 204. First ion injection pulse 208 also has a first pulse amplitude $A_1$ that is representative of the second voltage between wires 144 of ion gate device 118, that in the exemplary embodiment is substantially regulated to zero, i.e., ion gate device 118 is substantially de-energized. While ion gate device 118 is temporarily de-energized, a first portion of ions 114 are pulsed from ionization region 110 into a drift region 116 through ion gate device 118. The temporal period of de-energization is defined by first pulse width $W_1$.

Further, in operation, motion is induced in ions 114 as they exit ionization region 110 into drift region 116 when ion gate device 118 is de-energized and ions 114 are channeled through drift region 116 to detector 120. Signals representative of the ion population at detector 120 are generated and transmitted to spectral analysis device 122 to determine the constituents in the collected gas samples. The population of ions generated in ionization region 110 includes low-mobility analytes and high-mobility analytes. The low-mobility analytes traverse drift region 116 with a lower velocity than the high-mobility analytes due to the relatively greater molecular size of the low-mobility analytes as compared to the high-mobility analytes. As such, first spectral trace 255 is generated with the pair of peaks of resolved of high-mobility ion peaks 258. The voltage applied within ion gate device 118 is re-established, thereby substantially halting ion entry from ionization region 110 into drift region 116.

Moreover, in operation, second ion injection pulse 210 is transmitted from pulse control device 128 to ion gate device 118 as commanded by processing device 130. Second ion injection pulse 210 has second pulse width $W_2$ corresponding to a second temporal period on time axis 204. A value of second pulse width $W_2$ is greater than a value of first pulse width $W_1$, i.e., second ion injection pulse 210 is wider than first ion injection pulse 208. Second ion injection pulse 210 also has a second pulse amplitude $A_2$ that is representative of the second voltage between wires 144 of ion gate device 118, that in the exemplary embodiment is substantially regulated to zero, i.e., ion gate device 118 is substantially de-energized. While ion gate device 118 is temporarily de-energized, a second portion of ions 114 are pulsed from ionization region 110 into a drift region 116 through ion gate device 118. The temporal period of de-energization is defined by second pulse width $W_2$. The voltage applied between wires 144 of ion gate device 118 is again re-established, thereby substantially halting ion entry from ionization region 110 into drift region 116. Second spectral trace 255 is generated with second low-mobility ion peak 266. This alternating sequence of de-energizing and re-energizing ion gate device 118 through the use of pulses 208 and 210 is performed substantially continuously with a predetermined pulse frequency.

The pulse widths $W_1$ and $W_2$ for injection pulses 208 and 210, respectively, will vary according to different detector lengths and the associated applied drift voltages, and according to the different ion mobilities to be detected. The range of widths will extend from approximately 50 microseconds to approximately 500 microseconds for a substantial portion of the analytes of interest. The associated pulse repetition frequencies will vary for the same reasons. The temporal period between the narrower injection pulse 208 and the wider injection pulse 210 will be less than the return time back to narrower injection pulse 208 from pulse 210. These temporal periods will range between approximately 10 milliseconds (mS) and approximately 100 mS. Therefore, a full cycle of pulses 208 and 210 extends between approximately 5 hertz (Hz) and 50 Hz.

Also, TOF-IMS detection system 100 is not limited to any one polarity, i.e., system 100 is configured to operate with negative polarities and positive polarities. Shutter voltages between wires 144 of ion gate device 118 are within in a range of approximately 20 volts (V) and approximately 100 V and depend on the axial field in the instrument including system 100 and the wire spacing of gate 142 of ion gate device 118 (0.7 mm in the exemplary embodiment).

Further, TOF-IMS detection system 100 is not limited to just two different pulses and pulse widths. Rather, system 100 is configured to generate as many pulses with as many widths as necessary to enhance detection of as many analytes as required. For example, and without limitation, longer pulses facilitates detection of even larger and slower analytes with the condition that more pulses and longer pulses per cycle will take up additional sample time.

Data storage device 132 receives the spectral data associated with each spectrum of spectra 250 and stores it within data records therein. The spectra data records include data elements such as, and without limitation, pulse widths (for slow and fast ions) and polarities (positive and negative).

The IMS detection systems described herein provide a cost-effective system and method for improving detection of materials of interest from an object or person. The systems and methods described herein use two different pulse widths to inject ions from an ionization region into a drift region during de-energization of an ion gate device. The first, i.e., narrower pulse width facilitates de-energizing the ion gate device for a shorter temporal period, thereby enhancing detection of high-mobility ions through generating a first spectral trace including a plurality of resolved high-mobility ion peaks. As such, resolution of spectral traces of high-mobility analytes is enhanced. The same first spectral trace includes a low-mobility ion peak having a first amplitude. The second, i.e., wider pulse width facilitates de-energizing the ion gate device for a longer temporal period, thereby enhancing detection of low-mobility ions through generating a spectral trace including a low-mobility ion peak having a second amplitude greater than the first amplitude. As such, sensitivity for low-mobility analytes is also enhanced.

A technical effect of the systems and methods described herein includes at least one of: (a) enhancing resolution of high-mobility analytes in a TOF-IMS detection system while substantially simultaneously enhancing sensitivity of low-mobility ions by using two separate de-energization periods of the associated ion gate device of different temporal lengths.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of detecting constituents in a sample, said method comprising:
   channeling a sample gas stream to be tested for constituents into an ionization region;
   generating a plurality of ions in the ionization region;
   substantially preventing the plurality of ions in the ionization region from flowing into a drift region coupled to the ionization region through inducing a first voltage in a device positioned between the ionization region and the drift region; and
   injecting at least a portion of the ions from the ionization region into the drift region comprising:
      regulating the voltage in the device to a second voltage for a first predetermined temporal period, the second voltage less than the first voltage;
      regulating the voltage in the device to the first voltage; and
      regulating the voltage in the device to the second voltage for a second predetermined temporal period, the second predetermined temporal period different from the first predetermined temporal period.

2. The method in accordance with claim 1, wherein substantially preventing the plurality of ions in the ionization region from flowing comprises energizing an ion gate device.

3. The method in accordance with claim 1, wherein regulating the electric field to a second voltage comprises de-energizing an ion gate device.

4. The method in accordance with claim 1, wherein regulating the voltage in the device to a second voltage for a first predetermined temporal period comprises transmitting a first ion injection pulse having a first pulse width from a pulse control device to an ion gate device.

5. The method in accordance with claim 4, wherein transmitting a first ion injection pulse having a first pulse width comprises enhancing detection of high-mobility ions.

6. The method in accordance with claim 5, wherein enhancing detection of high-mobility ions comprises generating a first spectral trace including a plurality of resolved high-mobility ion peaks.

7. The method in accordance with claim 4, wherein regulating the voltage of the device to the second voltage for a second predetermined temporal period comprises transmitting a second ion injection pulse having a second pulse width from the pulse control device to the ion gate device, the second pulse width greater than the first pulse width.

8. The method in accordance with claim 7, wherein transmitting a second ion injection pulse having a second pulse width comprises enhancing detection of low-mobility ions.

9. The method in accordance with claim 8, wherein:
   transmitting a first ion injection pulse having a first pulse width to a pulse control device comprises generating a first spectral trace including a low-mobility ion peak having a first amplitude; and
   enhancing detection of low-mobility ions comprises generating the second spectral trace including a second low-mobility ion peak having a second amplitude greater than the first amplitude.

10. The method in accordance with claim 1, wherein injecting at least a portion of the ions from the ionization region into the drift region comprises alternating generation of ion spectra with the second voltage for the first predetermined temporal period and the second voltage for the second predetermined temporal period at a predetermined frequency.

11. An apparatus for detecting constituents in a sample, said apparatus comprising:
   a casing;
   an ionization region at least partially defined by said casing, said ionization region configured to generate ions;
   a drift region at least partially defined by said casing;
   an ion gate device positioned between said ionization region and said drift region, said ion gate device configured to facilitate prevention of the plurality of ions in said ionization region from flowing into said drift region through inducing a first voltage in said ion gate device; and a control system coupled to said ionization chamber, said control system comprising a processor, said control system configured to:
regulate the voltage in said ion gate device to a second voltage for a first predetermined temporal period and inject a first portion of the ions from said ionization region into said drift region, the second voltage less than the first voltage;
regulate the voltage in said ion gate device to the first voltage; and
regulate the voltage in said ion gate device to the second voltage for a second predetermined temporal period and inject a second portion of the ions from said ionization region into said drift region, the second predetermined temporal period different from the first predetermined temporal period.

12. The apparatus in accordance with claim 11 further comprising:
an ion detector positioned downstream of said drift region; and
a spectral analysis device coupled to said ion detector, said spectral analysis device configured to generate a detection spectrum representative of ions detected at said ion detector.

13. The apparatus in accordance with claim 12, wherein:
said control system further comprises a pulse control device coupled to said processing device, said control system further configured to transmit a first ion injection pulse having a first pulse width from said pulse control device to said ion gate device, thereby enhancing detection of high-mobility ions by said ion detector; and
said spectral analysis device configured to generate a first spectral trace including a plurality of resolved high-mobility ion peaks.

14. The apparatus in accordance with claim 13, wherein:
said control system further configured to transmit the first ion injection pulse having the first pulse width from said pulse control device to said ion gate device, thereby facilitating generation of a first spectral trace including a low-mobility ion peak having a first amplitude; and
said control system further configured to transmit a second ion injection pulse having a second pulse width from said pulse control device to said ion gate device, thereby enhancing detection of the low-mobility ions by said ion detection through generation of a second spectral trace including a second low-mobility ion peak having a second amplitude greater than the first amplitude.

15. The apparatus in accordance with claim 11, wherein said ion gate device configured to de-energize to inject the first portion of the ions and the second portion of the ions from said ionization region into said drift region.

16. The apparatus in accordance with claim 11, wherein said control system further comprises a pulse control device coupled to said processing device and said ion gate device, said processing device further configured to regulate the voltage in said ion gate device to the second voltage for the first predetermined temporal period through transmission of a first ion injection pulse having a first pulse width from said pulse control device to said ion gate device.

17. The apparatus in accordance with claim 16, wherein the second predetermined temporal period is different from the first predetermined temporal period, said control system further configured to transmit a second ion injection pulse having a second pulse width from said pulse control device to said ion gate device, the second pulse width greater than the first pulse width.

18. The apparatus in accordance with claim 11, wherein said control system further configured to alternate generation of ion spectra with the second voltage for the first predetermined temporal period and the second voltage for the second predetermined temporal period at a predetermined frequency.

19. One or more computer readable storage media having computer-executable instructions embodied thereon, wherein when executed by at least one processor, the computer-executable instructions cause the processor to:
regulate a voltage generated in an ion gate device to a first voltage, the ion gate device positioned between an ionization region and a drift region in an ion mobility spectrometer (IMS) detection system, thereby facilitating prevention of a plurality of ions flowing from the ionization region;
regulate the voltage generated in the ion gate device to a second voltage for a first predetermined temporal period, the second voltage less than the first voltage, thereby facilitating injection of a first portion of the ions from the ionization region into the drift region;
regulate the electric field to back to the first voltage; and
regulate the electric field to the second voltage for a second predetermined temporal period, thereby facilitating injection of a second portion of the ions from the ionization region into the drift region, the second predetermined temporal period different from the first predetermined temporal period.

20. The one or more computer readable storage media in accordance with claim 19, wherein when executed by at least one processor, the computer-executable instructions further cause the processor to:
transmit a first ion injection pulse having a first pulse width from a pulse control device to the ion gate device, thereby enhancing detection of high-mobility ions with an ion detector positioned downstream of the drift region through generating a first spectral trace including a plurality of resolved high-mobility ion peaks with a spectral analysis device coupled to the ion detector, the spectral analysis device configured to generate a detection spectrum representative of ions detected at the ion detector, and thereby generating the first spectral trace including a first low-mobility ion peak having a first amplitude; and
transmit a second ion injection pulse having a second pulse width from the pulse control device to the ion gate device, the second pulse width greater than the first pulse width, thereby enhancing detection of low-mobility ions through generating a second spectral trace including a second low-mobility ion peak having a second amplitude greater than the first amplitude.

* * * * *